US008669075B2

(12) United States Patent
Kim et al.

(10) Patent No.: US 8,669,075 B2
(45) Date of Patent: Mar. 11, 2014

(54) METHOD FOR THE IMMOBILIZATION OF BIOLOGICALLY ACTIVE POLYPEPTIDES BY USING MALTOSE BINDING PROTEIN

(75) Inventors: Sang-Heon Kim, Seoul (KR); Soo Hyun Kim, Seoul (KR); Min Han, Seoul (KR)

(73) Assignee: Korea Institute of Science and Technology, Seoul (KR)

(*) Notice: Subject to any disclaimer, the term of this patent is extended or adjusted under 35 U.S.C. 154(b) by 800 days.

(21) Appl. No.: 12/258,072

(22) Filed: Oct. 24, 2008

(65) Prior Publication Data

US 2010/0028950 A1  Feb. 4, 2010

(30) Foreign Application Priority Data

May 19, 2008  (KR) .................. 10-2008-0046180

(51) Int. Cl.
*C12P 25/00* (2006.01)
*A23J 1/00* (2006.01)

(52) U.S. Cl.
USPC ........................................ 435/69.7; 530/412

(58) Field of Classification Search
None
See application file for complete search history.

(56) References Cited

U.S. PATENT DOCUMENTS

2003/0027214 A1* 2/2003 Kamb ........................ 435/7.1

FOREIGN PATENT DOCUMENTS

| JP | 2002-537564 U | 11/2002 |
| JP | 2006-507834 A | 3/2006 |
| WO | 2004/050111 A2 | 6/2004 |

OTHER PUBLICATIONS

Geuijen et al., Identification and Characterization of Heparin Binding Regions of the Fim2 Subunit of *Bordetella pertussis*, Infection and Immunity, 1998, vol. 66, pp. 2256-2263.*
USMA Metric system temperature (last viewed on Dec. 14, 2010).*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
pMAL-c2x Vector description (last viewed on Dec. 14, 2010).*
Dijkmans et al., Characterization of platelet-derived growth factor-C (PDGF-C): expression in normal and tumor cells, biological activity and chromosomal localization., The International Journal of Biochemistry & Cell Biology., 2002, vol. 34, pp. 414-426.*
"Protocalsonline western blot" (last viewed on May 17, 2011).*

(Continued)

*Primary Examiner* — Alexander Kim
(74) *Attorney, Agent, or Firm* — Ladas & Parry LLP

(57) ABSTRACT

The present invention relates to a method for immobilization of a biologically active polypeptide using maltose binding protein (MBP) and a biologically active solid substrate on which a biologically active polypeptide is immobilized by the above method. More particularly, the present invention relates to a method for immobilization of a biologically active polypeptide comprising the following steps; 1) preparing a fusion protein by linking a biologically active polypeptide to carboxyl terminal of maltose binding protein (MBP); and 2) immobilizing the fusion protein on the hydrophobic surface by physical adsorption of amino terminal containing hydrophobic domain exposed on the surface of maltose binding protein on the hydrophobic surface of a solid substrate, and a biologically active solid substrate on which a biologically active polypeptide is immobilized by the said method.

14 Claims, 7 Drawing Sheets

1. MBP
(before loading on amylose resin)

2. MBP
(after loading on amylose resin)

3. MBP-VEGF
(before loading on amylose resin)

4. MBP-VEGF
(after loading on amylose resin)

(56) References Cited

OTHER PUBLICATIONS

Fernandez et al., Potential Role for Toll-Like Receptor 4 in Mediating *Escherichia coli* Maltose-Binding Protein Activation of Dendritic Cells, Infect Immun., E pub Jan. 12, 2007, vol. 75, pp. 1359-1363.*

Ito et al., Culture of human umbilical vein endothelial cells on immobilized vascular endothelial growth factor., Journal of Biomedical Materials Research Part A, 2005, vol. 74A, Issue 4, pp. 659-665.*

Nagohori et al., Glycosyltransferase Microarray Displayed in the Glycolipid LB Membrane., Adv. Synth. Catal. 2003, vol. 345, pp. 729-734.*

Eing et al., Quantification of the Raf-C1 Interaction With Solid-Supported Bilayers., ChemBioChem, 2002, vol. 3, pp. 190-197.*

Sehr et al. (2001). "A Generic Capture ELISA for Recombinant Proteins Fused to Glutathione S-Transferase: Validation for HPV Serology." J. Immuno. Methods, 253:153-162.

Ogiwara, et al. (2005). "Construction of a Novel Extracellular Matrix Using a New Genetically Engineered Epidermal Growth Factor Fused to IgG-Fe." Biotechnology Letters, 27:1633-1637.

Smyth et al. (2003). "Crystal Structures of Fusion Proteins with Large-Affinity Tags." Protein Sci., 12:1313-1322.

Lee, et al., (2007). "Direct Immobilization of Protein G Variants with Various Numbers of Cysteine Residues on a Gold Surface." Anal. Chem., 79:2680-2687.

Nagaoka, et al. (2006). "E-Cadherin-Coated Plates Maintain Pluripotent ES Cells Without Colony Formation." PLoS ONE (www.plosone.org), 1(e15):1-7.

Ogiwara, et al. (2006). "Effect of Photo-Immobilization of Epidermal Growth Factor on the Cellular Behaviors." Biochemical and Biophysical Research Communications, 345:255-259.

Anderson, et al. (2005). "Quartz Crystal Microbalance—With Dissipation Monitoring (QCM-D) for Real Time Measurements of Blood Coagulation Density and Immune Complement Activation on Artificial Surfaces." Biosensors and Bioelectronics, 21:79-86.

Fox, et al., (2001). "Single Amino Acid Substitutions on the Surface of *Escherichia coli* Maltose-Binding Protein Can Have a Profound Impact on the Solubility of Fusion Proteins." Protein Science, 10:622-630.

Qin, et al., (2007). "Two Methods for Glass Surface Modification and Their Application in Protein Immobilization." Colloids Surf. B: Bbiointerfaces, doi:10.1016/j.colsurfb.2007.06.018, 60:243-249.

Cecile A. W. Geuijen, et al; "Indentification and Characterization of Heparin Binding Regions of the Fim2 Subunit *Bordetella pertussis*", Infection and Immunity, May 1998, p. 2256-2263, vol. 66, No. 5.

David F. Carney, et al; "Site-specific mutations in the N-terminal region of human C5a that affect interactions of C5a with the neurtrophil C5a receptor", Protein Science (1993), 2, pp. 1391-1399, Cambridge University Press.

Joyce Dijkmans, et al; "Characterization of platelet-derived growth factor-C (PDGF-C): expressions in normal and tumor cells, biological activity and chromosomal localization", The International Journal of Biochemistry & Cell Biology 34 Apr. 2002, pp. 414-426.

* cited by examiner

1. MBP (before loading on amylose resin)
2. MBP (after loading on amylose resin)
3. MBP-VEGF (before loading on amylose resin)
4. MBP-VEGF (after loading on amylose resin)

```
                            SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Synthetic construct:  VEGF specific forward
      primer(VEGF-F)

<400> SEQUENCE: 1
ccgaattcgc acccatggca gaaggagg                                            28

<210> SEQ ID NO 2
<211> LENGTH: 28
<212> TYPE: DNA
<213> ORGANISM: Artificial Sequence
<220> FEATURE:
<223> OTHER INFORMATION: Synthetic construct:  VEGF specific reverse
      primer(VEGF-R)

<400> SEQUENCE: 2
acaagctttc accgcctcgg cttgtcac                                            28
```

METHOD FOR THE IMMOBILIZATION OF BIOLOGICALLY ACTIVE POLYPEPTIDES BY USING MALTOSE BINDING PROTEIN

TECHNICAL FIELD

The present invention relates to a method for immobilization of a biologically active polypeptide on the hydrophobic surface of a solid substrate by using maltose binding protein (MBP) as a linker and a biologically active solid substrate on which biologically active polypeptides are immobilized by the said method.

BACKGROUND ART

Immobilization of a protein has been widely applied in diagnosis and other fields such as biosensor or enzyme reactor. As methods to immobilize a protein, chemical cross-linking using a cross-linking agent such as glutaraldehyde, physical adsorption using hydrophobic binding, and chemical coupling using amine reactive group have been known. The biggest problem that these methods have to overcome is to maintain the activity of a protein or polypeptide supposed to be immobilized. For the chemical cross-linking or coupling, the activity might be inhibited by new chemical bonds or changes in chemical properties of a target protein by such bonds. For the physical adsorption, when a target protein is adsorbed on the hydrophobic surface directly, the structure of the protein might be changed to cause denaturation. To solve the above problems, immobilization using a linker has been tried, in which a linker binds to a polypeptide, the target of immobilization, as an immobilization mediator (Lee J. M. et al., *Anal. Chem.* 79: 2680-2687, 2007; Ogiwara K. et al., *Biochem. Biophy. Res. Comm.* 345: 255-259, 2006; Nagaoka M. et al., *PLoS ONE* 1: e15, 2006). The most representative method to bind a linker to a biologically active polypeptide is to synthesize a recombinant fusion protein based on genetic engineering techniques. For example, glutathione molecule capable of recognizing glutathione-S-transferase (GST) is pre-conjugated on the surface for enzyme-linked immunosorbent assay (ELISA) (Sehr P. et al., *J. Immuno. Methods.* 253: 153-162, 2001). However, this method is not effective for non-reactive hydrophobic surface such as polystyrene because glutathione is difficult to bind to such non-reactive hydrophobic surface.

In the meantime, another method has been made using a linker having a hydrophobic domain, which was to increase efficiency in adsorption of a protein and at the same time to prevent denaturation thereof so as to maintain biological functions of the target protein after adsorption and thus to be ready for use as the surface for cell culture. A linker for the fusion protein immobilization based on hydrophobic binding is selected among those proteins having a strong hydrophobicity such as Fc domain of immunoglobulin (Ogiwara K. et al., *Biotech. Letters* 27: 1633-1637, 2005; Nagaoka M. et al., *PLoS ONE* 1: e15, 2006) and hydrophobin (Qin M. et al., *Colloids Surfaces* 60: 243-249, 2007). This linker facilitates adsorption without requiring a pre-surface treatment.

For example, EGF-Fc or cadherin-Fc is fixed on a polystyrene culture dish to prepare EGF or cadherin adsorbed surface, and then epithelial tumor cells or embryonic stem cells are cultured thereon. Then, the cells demonstrate different biochemical and cell-biological characteristics (Ogiwara K. et al., *Biotech. Letters* 27: 1633-1637, 2005; Nagaoka M. et al., *PLoS ONE* 1: e15, 2006). Alternative binding methods have been reported. For example, U.S. Patent No. 20040235050 describes a protein immobilization method using hydrophobin for the conjugation of an enzyme onto the hydrophobic surface. However, when Fc and hydrophobin are used, carboxy-terminal of Fc and hydrophobin is necessarily adsorbed onto the hydrophobic surface and then amino terminal of Fc and hydrophobin has to bind with a biologically active target polypeptide. So, if it is the case that carboxy terminal is necessary for the activation of a biologically active target polypeptide, these methods are not appropriated. In addition, the linker region of a fusion protein for hydrophobic binding is mostly originated from animals and fungi, so that when it is expressed in *E. coli* and purified from it, inclusion body formation would be a problem.

Thus, the present inventors tried to solve the problems of the conventional methods. As a result, the present inventors completed this invention by confirming that a biologically active polypeptide fusion protein can be prepared by using maltose binding protein facilitating the expression and purification in *E. coli* owing to its excellent maltose binding capacity, and when this fusion protein is fixed by simple physical adsorption on the hydrophobic surface such as polystyrene by using the hydrophobic domain of maltose binding protein (Fox J. D. et al., *Protein Science* 10: 622-630, 2001), the biologically active polypeptide of the fusion protein still retains its biological activities.

DISCLOSURE

Technical Problem

It is an object of the present invention to provide a method for immobilization of a biologically active polypeptide such as cytokine or a specific growth factor on the hydrophobic surface of a solid substrate by simple physical adsorption without any pre-treatment by using maltose binding protein having a hydrophobic domain, which facilitates the expression in *E. coli* and the purification therefrom, and to provide a biologically active solid substrate on which a biologically active polypeptide is immobilized by the said method.

Technical Solution

To achieve the above object, the present invention provides a method for immobilization of a biologically active polypeptide on a solid substrate, which comprises the following steps:

1) preparing a fusion protein by linking a biologically active polypeptide to carboxyl terminal of maltose binding protein (MBP); and 2) immobilizing the fusion protein on the hydrophobic surface by physical adsorption of amino terminal containing hydrophobic domain exposed on the surface of maltose binding protein on the hydrophobic surface of a solid substrate.

The present invention also provides a biologically active solid substrate on which a biologically active polypeptide is immobilized by using maltose binding protein as a linker.

The present invention further provides a use of maltose binding protein for the preparation of the biologically active solid substrate.

Hereinafter, the present invention is described in detail.

The present invention provides a method for immobilization of a biologically active polypeptide on a solid substrate, which comprises the following steps:

1) preparing a fusion protein by linking a biologically active polypeptide to carboxyl terminal of maltose binding protein (MBP); and 2) immobilizing the fusion protein on the hydrophobic surface by physical adsorption of amino terminal containing hydrophobic domain exposed on the surface of maltose binding protein on the hydrophobic surface of a solid substrate.

In step 1) of the above method, a nucleotide sequence encoding a biologically active polypeptide is fused to carboxyl terminal of a nucleotide sequence encoding maltose binding protein and the fragment of the above fusion gene is introduced into E. coli, expressed therein and purified therefrom to give a fusion protein composed of maltose binding protein and a biologically active polypeptide.

The maltose binding protein (MBP) is a protein located in periplasm crossing cell membrane of E. coli, which is precisely a periplasm protein involved in migration of saccharides such as maltose or maltodextrin. Maltose binding protein is largely used to produce a useful foreign protein as a fusion protein form. This protein is translated from malE, an intracellular gene. If a foreign protein gene is inserted in downstream of a cloned malE gene and expressed in cells, a fusion protein composed of two proteins can be mass-produced. Particularly, if the size of a target protein is small or a target foreign protein becomes less stable in different host cells, the target protein is preferably expressed in cells as a fusion protein combined with maltose binding protein. A foreign protein expressed from malE binding gene can be separated by taking advantage of maltose-affinity of maltose binding protein. For example, a resin coated with amylose, the form of multiple maltose, is reacted with cell lysate. The reacted resin is washed several times to eliminate non-targeted proteins. The target protein can be eluted by adding high concentration of maltose. Therefore, maltose binding protein can be used to mass-express a target protein in cells, which can be easily separated and purified. So, the expression system expressing the fusion protein binding to maltose binding protein is world-widely used for the production of a target foreign protein.

In step 1) of the method of the present invention, a fusion protein where maltose binding protein is fused to a biologically active target polypeptide is produced by taking advantage of characteristics of maltose binding protein. Particularly, the step can include the following steps: (i) preparing a fusion gene fragment encoding the fusion protein produced by linking a biologically active target polypeptide to carboxyl terminal of maltose binding protein; (ii) constructing an expression vector containing the fusion gene fragment; (iii) generating a transformed microorganism transfected with the expression vector; and (iv) expressing and purifying the fusion protein from the transformed microorganism.

First, a nucleotide sequence encoding a biologically active target polypeptide is fused to carboxyl terminal of a nucleotide sequence encoding maltose binding protein to produce a fusion gene fragment.

According to the method of the present invention, the biologically active target polypeptide is fused to carboxyl terminal of maltose binding protein for the production of a fusion protein. In the meantime, amino terminal containing hydrophobic domain exposed on the surface is used for physical adsorption onto the hydrophobic surface thereafter.

The biologically active target polypeptide of the present invention can be a random polypeptide that is biologically active or can be fused to one or more target molecules. The amino terminal of such polypeptide can include a polypeptide which is not necessary for biological activities. This protein can be exemplified by antigen, antibody, enzyme, structural protein, adhesion protein or regulatory protein, but not always limited thereto.

Such biologically active polypeptide genes have a great importance in the fields of human medicine and industry. These genes can be separated from various plants and animals including human and microorganism genes for recombination or can be chemically synthesized to encode the polypeptides. A part or the entire nucleotide sequence of such gene encoding a biologically active polypeptide is fused to ORF (open reading frame) of carboxyl terminal of maltose binding protein, and as a result, a fusion gene fragment is produced.

To express the recombinant fusion gene fragment prepared above, a recombinant expression vector is constructed by inserting this gene fragment in an expression vector for E. coli. The expression vector for E. coli herein is not limited and any expression vector capable of expressing a foreign gene in E. coli can be used.

In a preferred embodiment of the present invention, as a biologically active polypeptide, vascular endothelial growth factor (VEGF) was amplified by PCR and the amplified VEGF gene was cloned into a vector containing maltose binding protein gene to construct an expression vector containing the fusion protein where VEGF gene was linked to carboxyl terminal of maltose binding protein.

E. coli was transfected with the recombinant expression vector produced according to the present invention and the transformed E. coli was cultured to express the fusion protein of maltose-binding protein-biologically active polypeptide. When $OD_{600}$ of the culture solution reached 0.3-0.6, IPTG was added at the final concentration of 0.1-3 mM, followed by further culture for 2-6 hours. The expressed fusion protein was separated and purified from the E. coli culture solution. And the method for the separation and purification herein was affinity chromatography using maltose specific material such as amylose resin having specific affinity to maltose.

In this method, step 2) is the process of immobilization of the fusion protein of maltose binding protein-biologically active polypeptide on the hydrophobic surface. The immobilization is accomplished by physical adsorption using hydrophobic domain exposed on the surface of amino terminal of maltose binding protein in the fusion protein as a linker.

Particularly, the fusion protein was diluted in a proper buffer, for example buffered phosphate saline (PBS), Tween 20/PBS, Tris-HCl buffer, or bicarbonate buffer, at the concentration of 1 ng/Ml-0.5 mg/Ml. This diluted solution was applied on the hydrophobic surface, followed by reaction at 4-25° C. for 1-24 hours. As a result, the hydrophobic domain of amino terminal of maltose binding protein was adsorbed on the hydrophobic surface by physical adsorption, leading to the immobilization of the fusion protein on the hydrophobic surface.

The proper hydrophobic surface of the present invention can be exemplified by silanized surface, carbon nanotube (CNT) surface, hydrocarbon coated surface, polymer (polystyrene, polycarbonate, polypropylene, polyethylene, teflon, polytetrafluoroethylene or polyester containing biodegradable polymer, etc) surface or metal (stainless steel, titanium, gold, platinum, etc), but not always limited thereto.

The fusion protein immobilized on such hydrophobic surface plays an important role in regulation of cell functions because its biologically active polypeptide region which is important for cell recognition is exposed outside so that it can be easily linked to a receptor exiting on cell membrane to regulate the functions. Besides, the biologically active polypeptide of the fusion protein immobilized on the hydrophobic surface retains its original biological activities including enzyme activity, catalytic activity, antigen specificity and regulation activity. In this invention, 'retain the original biological activities' indicates that the biologically active polypeptide still retains its original biological activities or functions at least 50%, preferably at least 60% and more preferably at least 70% after the fusion with maltose binding protein. It is more preferred that the fused biologically active polypeptide herein retains its original biological activities at least 80% and most preferably at least 90%.

The present invention also provides a biologically active solid substrate on which a biologically active polypeptide is immobilized by using maltose binding protein as a linker according to the said method.

The present invention also provides a biologically active solid substrate on which a biologically active polypeptide is immobilized by using maltose binding protein as a linker.

The present invention further provides a use of maltose binding protein for the preparation of the biologically active solid substrate.

The biologically active solid substrate herein not only facilitates interaction between a biologically active polypeptide having a specific biological activity, exposed on the surface of the solid substrate, and a target molecule or cell receptor but also can be applied in different uses according to the biologically active polypeptides having different biological activities fixed on the surface. The most common use of the biologically active solid substrate of the present invention is for cell culture. Particularly, a biologically active polypeptide required for a specific cell culture is immobilized on a hydrophobic cell culture vessel substrate by using maltose binding protein according to the immobilization method of the present invention. If cells are cultured on the culture vessel, culture will be more efficient because of direct interaction between the cells and the biologically active polypeptide. So, if cells are cultured on a biologically active solid substrate on which a biologically active polypeptide is immobilized, the biological activity of the fused polypeptide causes changes in intracellular signal transduction and induces cell morphology and functional changes. Therefore, this method can be effectively used in the field of regenerative medicine, for example, for the study of stem cell differentiation and tissue engineering, and for the study of cell censor or cell chip, etc.

The cell culture method using a biologically active solid substrate of the present invention can also be used for the following purposes; direct cell adhesion of a biologically active polypeptide exposed as being fixed by maltose binding protein on the hydrophobic surface; indirect cell adhesion together with a natural extracellular matrix (ECM) such as collagen, fibronectin and laminin; or application of the immobilized biologically active polypeptide in cell signal transduction, etc.

The biologically active solid substrate of the present invention can also be applied in diagnostic devices. For example, the substrate can be used as a biosensor, precisely a biologically active target polypeptide is immobilized on hydrophobic strips or microtiter surface by using maltose binding protein as a linker, resulting in the preparation of a biosensor.

As explained hereinbefore, the preparation of a biologically active solid substrate by immobilizing a biologically active polypeptide by using maltose binding protein facilitates the studies on the interaction between the immobilized active polypeptide and another polypeptide and thus it can be effectively applied in high-throughput screening, solid phase extraction or purification with chromatography.

Advantageous Effect

According to the method for immobilization of a biologically active polypeptide of the present invention, a biologically active polypeptide can be immobilized on the hydrophobic surface of a solid substrate by simple physical adsorption using the hydrophobic domain of maltose binding protein, the periplasm protein, as a linker with maintaining the biological activity of the active polypeptide. Such solid substrate having a biologically active polypeptide immobilized thereon has an advantage of wide application including the fields of regenerative medicine, specifically for cell culture, studies of stem cell differentiation, and tissue engineering, and the fields of studies on cell sensor or cell chip.

DESCRIPTION of DRAWINGS

The application of the preferred embodiments of the present invention is best understood with reference to the accompanying drawings, wherein.

MODE FOR INVENTION

Figure 1:
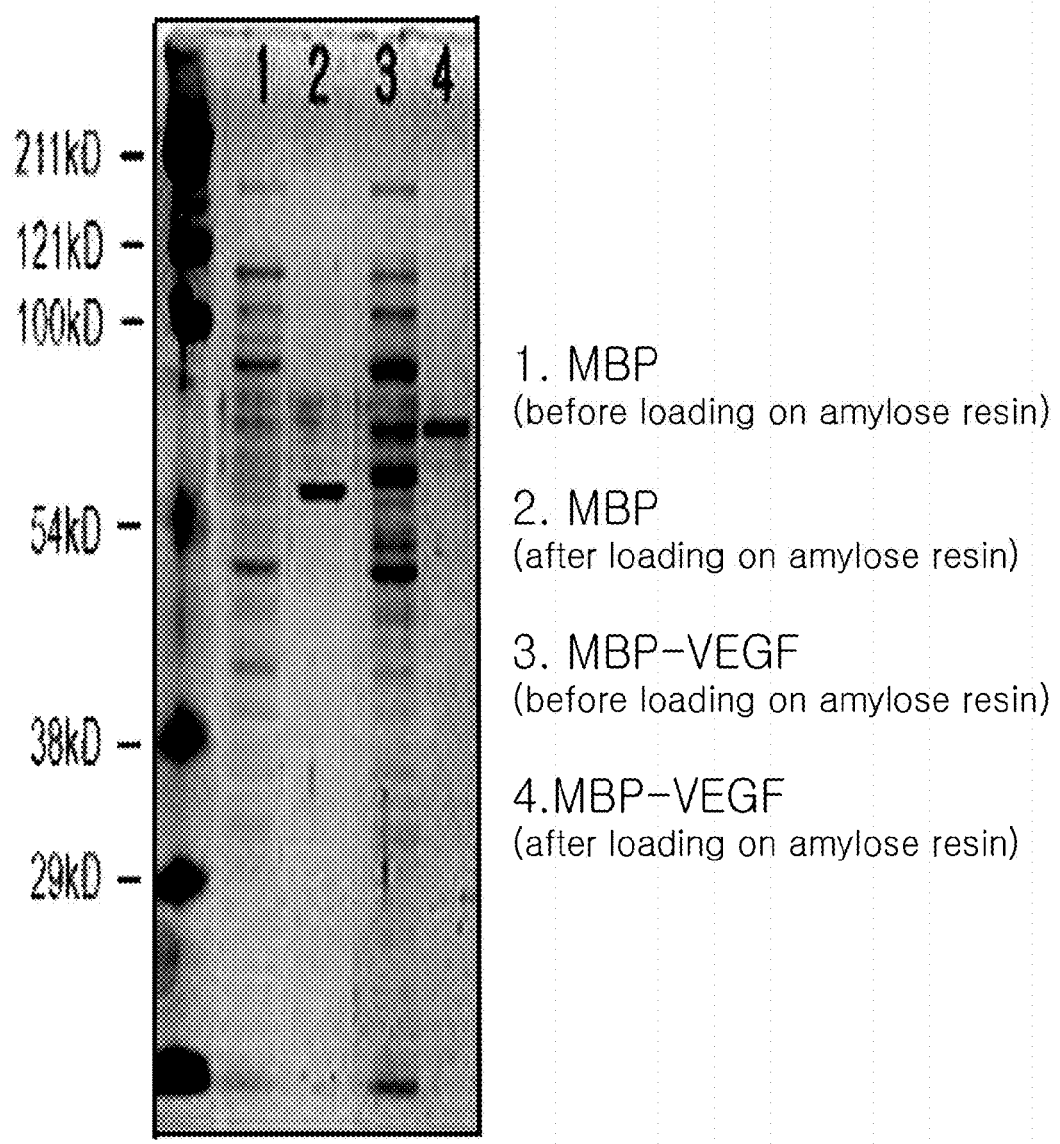
FIG. 1 is a diagram showing the result of SDS-PAGE with the recombinant fusion protein MBP-VEGF comprising maltose binding protein (MBP) and vascular endothelial growth factor (VEGF)

Practical and presently preferred embodiments of the present invention are illustrative as shown in the following Examples.

However, it will be appreciated that those skilled in the art, on consideration of this disclosure, may make modifications and improvements within the spirit and scope of the present invention.

Reference Example 1

DNA Fragmentation with Restriction Enzyme and Recovery of the Fragments

The restriction enzyme and buffer used in this example were purchased from Enzynomics Co. Reaction was induced in a sterilized 1.5 Ml eppendorf tube with the reaction volume of 20-30 µl at 37° C. for 4-5 hours. The composition of 10× buffer used for the restriction enzyme reaction was as follows:

1) 10× Enzynomics buffer Ez buffer I: 100 mM Tris-HCl (pH 7.5, 25° C.), 50 mM NaCl, 10 mM $MgCl_2$, 0.025% Triton X-100, and 2) 10× Enzynomics buffer Ez buffer II: 10 mM Tris-HCl (pH 7.5, 25° C.), 50 mM NaCl, 10 mM $MgCl_2$, 1 mM dithiothreitol.

To recover the DNA fragments, the electrophoresed agarose gel was irradiated by UV transilluminator (Avegene) and gels containing the DNA fragments were collected by cutting. Then, the fragments were isolated by using gel extraction kit (Qiagene).

Reference Example 2

Treatment of Bacterial Alkaline Phosphatase

BAP solution used for the treatment of bacterial alkaline phosphatase (BAP) was purchased from Fermentas Co. Reaction was induced in a sterilized 1.5 Ml eppendorf tube with the reaction volume of 50 µl at 60-65° C. for 1 hour. 1 M Tris-HCl buffer (pH 8.0; Bioneer) was used for the BAP reaction.

Reference Example 3

Ligation Reaction

Ligation reaction was performed using DNA ligation kit (DNA Ligation Kit Ver 2.1, Takara), for which a vector and an insert were mixed at the ratio of 1:3 and the reaction volume was adjusted to 10-20 µl. The reaction was induced at 16° C. at least for 12 hours.

Reference Example 4

Transformation of E. coli

E. coli K12 TB1 (New England Biolabs) was used as a host cell for the transformation. The cells were inoculated in 60 Ml of liquid medium (10 g/L bacto-tryptone, 5 g/L yeast extract, 10 g/L NaCl), followed by shaking-culture at 37° C. until $OD_{600}$ reached 0.4-0.6. The cultured cells were loaded in a 1.5 Ml eppendorf tube, followed by centrifugation to harvest the cells. 300 µl of 50 mM $CaCl_2$ was added to the harvested cells, followed by moderate vortexing. To harvest the cells, centrifugation was performed again. 300 µl of 50 mM $CaCl_2$ was added to the harvested cells to disperse the cells evenly, which stood at 0° C. for 30 minutes. Centrifugation was performed to eliminate the supernatant. The precipitated cells were evenly dispersed in 150 µl of cold solution comprising 50 mM $CaCl_2$ and 15% glycerol. The cell suspension was stored in a freezer.

Reference Example 5

Synthesis of Oligonucleotide

To amplify a gene encoding a biologically active target polypeptide, a primer set for polymerase chain reaction (PCR) was synthesized with oligonucleotide synthesis service provided by Bioneer.

Reference Example 6

Polymerase Chain Reaction 50 ng of a template and 10 µM of each forward primer and reverse primer were mixed with distilled water to make total volume of 10 µl, and then hot start PCR premix (Bioneer) was added thereto. PCR was performed as follows with the reaction mixture by using T-gradient thermo block (Applied Biometra); predenaturation at 95° C. for 1 minute, denaturation at 94° C. for 30 seconds, annealing at 55° C. for 30 seconds, polymerization at 68° C. for 1 minute, 31 cycles from denaturation to polymerization, and final extension at 72° C. for 5 minutes. The amplified product was purified with PCR purification kit (Bioneer), which proceeded to electrophoresis on agarose gel. The agarose gel was irradiated by UV transilluminator (Avegene) and gel containing the PCR product was recovered. The amplified DNA was isolated from the recovered gel fragment by using gel extraction kit (Qiagene).

Reference Example 7

Cell Culture

293/KDR cells originated from HEK293 human embryonic kidney cells are manipulated to express human VEGFR-2 (KDR/Flk1) receptor. The cells were purchased from Sibtech as 5-subcultured cells. The cells were cultured in DMEM liquid medium (Dulbecco's Modified Eagle's Medium, Welgene) (4500 mg/L D-glucose, L-glutamine, 110 mg/L sodium pyruvate, 10% FBS) supplemented with 0.375 µg/Ml puromysin (Sigma) in a 37° C. 5% $CO_2$ incubator (Thermo). The medium was replaced with a fresh one every other day. When the cells were grown 70-80% of T-flask, they were sub-cultured.

Reference Example 8

Preparation of 7.5% Polyacrylamide Gel 7.5% polyacrylamide gel was prepared by using Mini-protean 3 Electrophoresis Set (Bio-rad). First, a casting frame was prepared by fixing 1.0 mm glass plate in a frame. 4.94 Ml of distilled water, 2.5 Ml of 1.5 M Tris-HCl buffer, 2.5 Ml of acrylamide solution, 50 µl of 10% ammonium persulfate (APS) and 10 µl of TEMED (N,N,N',N'-tetra methyl ethylene diamine) were added in a 50 Ml conical tube. After mixing well, 4.5 Ml of the mixture was loaded on the 1.0 mm glass plate to prepare resolution gel. 500 µl of distilled water was added thereto not to dry the gel. When the resolution gel was completely hardened, distilled water on the gel was removed. To prepare stacking gel, 3.05 Ml of distilled water, 1.25 Ml of 0.5 M Tris-HCl buffer, 0.67 Ml of 30% acrylamide solution, 25 µl of 10% APS and 5 µl of TEMED were added in a 50 Ml conical tube. After mixing well, the mixture was loaded on the 1.0 mm glass plate, on which 15-well (20 µl) template was put, followed by solidification. Reagents used for the preparation of polyacrylamide gel were as follows:
1) 1.5 M Tris-HCl buffer: Tris base 18.17 g (Invitrogen), 20% SDS (Amersham Pharmacia Biotech) 2 Ml, distilled water 80 Ml, (pH 8.8),
2) 0.5 M Tris-HCl buffer: Tris base 6.06 g (Invitrogen), 20% SDS (Amersham Pharmacia Biotech) 2 Ml, distilled water 80 Ml, (pH 6.8), and
3) 30% acrylamide solution: 29% acrylamide (Sigma), 1% bis-acrylamide (Sigma).

Reference Example 9

Biotin Coupling

Biotin coupling of proteins was performed by using sulfo-NHS-biotinylation kit (Pierce). Proteins were diluted with phosphate buffered saline (PBS) to make the reaction volume of 0.5-2 Ml and at the final protein concentration of 1-10 mg/Ml. The concentration of 10 mM sulfo-NHS-biotin solution was calculated according to the molecular weight of the protein to be treated with biotin, which was added and reacted at room temperature for one hour. In the meantime, a 15 Ml conical tube was linked to desalt spin column included in the above sulfo-NHS-biotinylation kit, followed by centrifugation (Hanil) at 1000×g for 2 minutes. The solution stored in the conical tube was eliminated. 2.5 Ml of PBS was added to the desalt spin column, followed by centrifugation at 1000×g for 2 minutes to wash the desalt spin column. The washing was repeated twice. A new 15 Ml conical tube was linked to the desalt spin column, to which biotin-treated reactant was added, followed by centrifugation at 1000×g for 2 minutes to separate biotin conjugated proteins.

Example 1

Construction of a Plasmid pMAL-c2X-VEGF Expressing a Recombinant Protein

<1-1> Construction of a Plasmid Harboring VEGF Gene Cloned Therein

To construct a plasmid containing VEGF gene cloned therein, a forward primer VEGF-F (EcoRI) having a nucleotide sequence represented by SEQ. ID. NO: 1 and a reverse primer VEGF-R (HindIII) having a nucleotide sequence represented by SEQ. ID. NO: 2 were synthesized. PCR was performed using a whole gene extracted from human vascular smooth muscle (VSM) cells as a template with the primer set above to amplify only the 165 region of vascular endothelial growth factor (VEGF).

4 ng of the amplified VEGF gene fragment, 50 ng of pGEM-T vector and 1 µl of T4 DNA ligase were added to 5 µl of 2× ligation buffer included in pGEM-T vector system I (Promega). Then, distilled water was added until the total volume reached 10 µl. The mixture was stood at room temperature for one hour, followed by reaction at 16° C. for 12 hours. Upon completion of the reaction, E. coli K12 TB1 was transfected with the ligated product above, from which a recombinant plasmid containing a target gene cloned therein was selected and named 'pGEM-VEGF'.

<1-2> Construction of a Plasmid Harboring MBP-VEGF Fusion Gene Cloned Therein

To fuse the linker, maltose binding protein (MBP), with VEGF gene, the recombinant plasmid pGEM-VEGF constructed in Example <1-1> was digested with restriction enzymes EcoRI and HindIII in Enzynomics buffers Ez buffer I and Ez buffer II, leading to the isolation of VEGF gene fragments on agarose gel. The isolated VEGF gene fragments were treated with BAP to facilitate ligation reaction. For the BAP treatment, 7.5 µl of buffer (1 M Tris-HCl, pH 8.0, Bioneer) was mixed with 1 µl of BAP solution (Fermentas). VEGF gene was added thereto until the total volume reached 50 µl, followed by reaction at 65° C. for 1 hour. The reactant was electrophresed on agarose gel. The agarose gel was irradiated by UV transilluminator (Avegene) and gel containing the target fragment was recovered. The VEGF gene fragment was isolated from the recovered gel fragment by using gel extraction kit (Qiagene).

The vector harboring MBP gene for ligation, pMAL-c2X (New England Biolabs) was digested with EcoRI and HindIII in Enzynomics buffers Ez buffer I and Ez buffer II, followed by separation of the fragments of MBP containing vector on agarose gel.

9 µl of the VEGF gene separated above, 3 µl of the digested vector fragment pMAL-c2X and 12 µl of enzyme solution I included in DNA ligation kit (Ver 2.1, Takara) were mixed. Distilled water was added thereto to make total volume 20 µl, followed by reaction at 16° C. for 16 hours. Upon completion of the reaction, E. coli K12 TB1 was transfected with the ligated product, from which a recombinant plasmid containing MBP-VEGF fusion gene cloned therein was screened and then named 'pMAL-c2X-VEGF'.

Example 2

Expression and Purification of MBP-VEGF Fusion Protein

<2-1> Induction of MBP-VEGF Fusion Protein Expression

E. coli K12 TB1 was transfected with the recombinant plasmid pMAL-c2X-VEGF expressing MBP-VEGF fusion protein, followed by culture at 37° C. in LB (Luria-Bertani) solid medium for one day. Next day, colonies formed on the medium were recovered and inoculated in 3 Ml of RB (rich medium+glucose) liquid medium containing 60 µg/Ml ampicillin, followed by further culture at 37° C. for approximately 2 hours. IPTG (isopropyl-β-D-thiogalactopyranoside) was added thereto at the final concentration of 3 mM, followed by culture at 37° C. for 2 hours again. Upon completion of the culture, 1 Ml of the culture solution was centrifuged to obtain cell precipitate. 20 µl of 1× sample loading buffer was added to the cell precipitate, which was then well mixed. The mixture was boiled at 95° C. for 5 minutes and then cooled down to room temperature. 15 µl of the prepared solution proceeded to electrophoresis on 10% SDS-polyacrylamide gel. Upon completion of the electrophoresis, the polyacrylamide gel was stained with coomassie brilliant blue. Western blotting was performed using anti-MBP antiserum (New England Biolabs) to investigate the expression of MBP-VEGF fusion protein.

<2-2> Expression and Purification of Water-Soluble Fusion Protein

E. coli cells transfected with the recombinant plasmid pMAL-c2X-VEGF prepared in Example <2-1> were inoculated in RB medium containing 60 µg/Ml ampicillin, followed by culture for overnight at 37° C. 10 Ml of the culture solution was added to 1 l of RB medium, followed by shaking-culture at 37° C. When $OD_{650}$ of the culture solution reached approximately 0.6, IPTG was added at the final concentration of 3 mM. 2 hours after the IPTG treatment, culture was terminated. The culture solution was centrifuged (Combi-514R, Hanil) at 4000×g for 20 minutes to obtain cell precipitate. The cell precipitate was resuspended in 50 Ml of buffer (1 M Tris-HCl 20 Ml, pH 7.5, NaCl 11.7 g, 0.5 M EDTA 2 Ml), to which EDTA (ethylenediaminetetraacetic acid) and PMSF (phenylmethanesulphonyl fluoride) were added at the final concentration of 1 mM. The cell culture mixture was frozen (−20° C.) and thawed repeatedly before purification to make cell lysis easy. The cells were lysed by using sonic dismembrator (Fisher Scientific Model 500 Sonic Dismembrator) with 10% output for approximately 10 seconds in ice bath. Then, the cell lysate was stood in ice bath for 30 seconds. The above process was repeated twice for complete cell lysis. The cell homogenate obtained thereby was centrifuged (Combi-514R, Hanil) at 9000×g for one hour to obtain supernatant containing water-soluble protein, which was 5× diluted with buffer (1 M Tris-HCl 20 Ml, pH 7.5, NaCl 11.7 g, 0.5 M EDTA, 2 Ml)r.

To separate MBP-VEGF fusion protein expressed in E. coli transformed microorganism, affinity chromatography was performed using amylase resin (New England Biolabs). This column was equilibrated by washing with 8× bed volume buffer (1 M Tris-HCl 20 Ml, pH 7.5, NaCl 11.7 g, 0.5 M EDTA 2 Ml). The supernatant containing water-soluble protein obtained above was loaded in the equilibrated amylase resin affinity chromatography at the speed of 1 Ml per minute. Non-adsorbed proteins were removed by running with 12× bed volume buffer (1 M Tris-HCl 20 Ml, pH 7.5, NaCl 11.7 g, 0.5 M EDTA 2 Ml). The proteins adsorbed on the resin was eluted by adding 10 mM maltose elution buffer (1 M Tris-HCl 20 Ml, pH 7.5, NaCl 11.7 g, 0.5 M EDTA 2 Ml, 10 mM maltose) at the speed of 1 Ml per minute. The recovered protein proceeded to electrophoresis (Bio-rad) on 10% polyacrylamide gel, followed by examination of molecular weight and purify of the separated protein. As a result, the purified protein had at least 95% of purity and 60,000 Da of molecular weight.

The protein sample was placed in dialysis membrane (MWCO12-14,000, Spectrum laboratories, Inc.), followed by dilution with PBS for 3 days to obtain maltose-eliminated protein. Then, the protein was concentrated by centrifugation (Combi-514R, Hanil) at 4000×g for 45 minutes using Centrifugal Filter (Amicon Ultra-15 MWCO 5,000, Millipore). The concentrated protein was named 'MBP-VEGF'.

FIG. 1 illustrates the results of SDS-PAGE with MBP alone (lane 1) and MBP-VEGF fusion protein (lane 3) before loading on amylose resin, and purified MBP alone (lane 2) and MBF-VEGF fusion protein (lane 4) after loading on amylose resin. As shown in this Figure, MBP-VEGF fusion protein had higher molecular weight than MBP alone, suggesting that the fusion protein was expressed in *E. coli* transformed microorganism.

Example 3

Measurement of MBP-VEGF Fusion Protein Activity

<3-1> 293/KDR Phosphorylation Induced by MBP-VEGF Fusion Protein

To measure the activity of MBP-VEGF fusion protein, 293/KDR cells were cultured and the cultured cells were inoculated in a 6-well plate at the concentration of $5 \times 10^5$ cells/well. The 293/KDR cells indicated 293HEK cells (human embryonic kidney cells) over-expressing VEGFR2 (VEGF receptor), which have been used for VEGF phosphorylation test. 6 hours after the cell inoculation, the medium was replaced with DMEM liquid medium (Dulbecco's Modified Eagle's Medium, Welgene) supplemented with 0.05% FBS (fetal bovine serum, Welgene). 16 hours later, the medium was replaced with assay medium (DMEM, Welgene, 25 mM HEPES pH 7.2, Sigma, 5 mM $Na_3VO_4$, Sigma, 0.05% BSA (bovine serum albumin), Sigma), followed by culture in an incubator (Thermo) for 10 minutes.

To stimulate the 293/KDR cells, VEGF165 (vascular endothelial cell growth factor 165, R&D Systems) and MBP-VEGF fusion protein were diluted in the assay medium at different concentrations of 0, 1, 5, 10, 50 and 100 ng/Ml, respectively. The diluted VEGF and MBP-VEGF fusion protein were added to each group of the cultured 293/KDR cells by 1.5 Ml per group, followed by culture in a 37° C. incubator (Thermo) for 10 minutes. The cells stimulated by VEGF and MBP-VEGF fusion protein were put in ice and then washed with cold PBS twice. To lyse the cells, RIPA (Radio-Immunoprecipitation Assay, Pierce) buffer was mixed with 1 mM sodium orthovanadate (Sigma), 5 mM sodium pyrophosphate (Sigma) and 25 mM sodium fluoride (Sigma). 100 μl of the mixed solution was added to the cell reaction solution. The cells were recovered by using scrapper (SPL). The recovered cells of each group were put in ice for one hour, followed by centrifugation (micro 17TR, Hanil) at 15,000 rpm for 30 minutes to obtain supernatant. Protein in the supernatant was quantified by BCA (Pierce) protein quantification method. Each sample was added to 5× sample buffer (0.6 M 1 M Tris-HCl, pH 6.8, 5 Ml 50% glycerol, 2 Ml 10% SDS, 0.5 Ml 2-mercaptoethanol, 1 Ml 1% bromophenol blue, 0.9 Ml distilled water). The final concentration of each sample was adjusted evenly with distilled water, which was put in a 1.5 Ml eppendorf tube and stored at 4° C.

Figure 2:
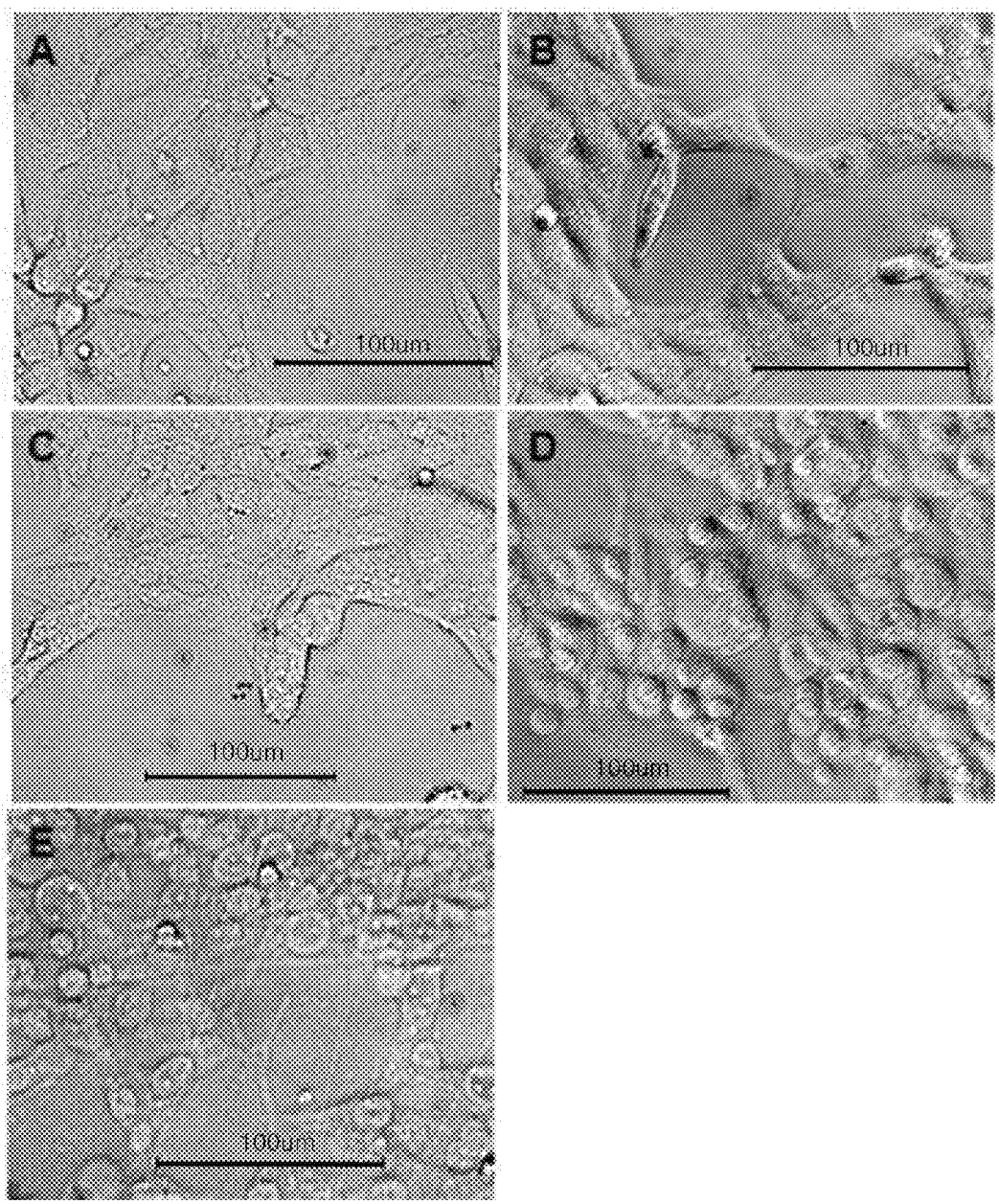
FIG. 2 is a diagram showing the morphological changes of 293/KDR cells treated with the MBP-VEGF fusion protein of the present invention according to concentrations of the fusion protein.

FIG. 2 illustrates the cell morphology before cell lysis. FIG. 2A illustrates the cell morphology before assay medium was added. FIG. 2B illustrates the cell morphology after treating assay medium for 10 minutes. FIG. 2C illustrates the cell morphology after treating MBP (100 ng/Ml) for 10 minutes. FIG. 2D illustrates the cell morphology after treating MBP-VEGF (150 ng/Ml) for 10 minutes. FIG. 2E illustrates the cell morphology after treating VEGF (50 ng/Ml) for 10 minutes. In the groups treated with assay medium and MBP (B and C), extended cell morphology was observed, similarly to that observed before the treatment. In the groups treated with MBP-VEGF and VEGF (D and E), the shape of cell was changed into round. The above results indicate that the VEGF activity is maintained when it is expressed and purified as MBP-VEGF fusion protein.

<3-2> Changes of 293/KDR Phosphorylation Signal by MBP-VEGF Fusion Protein

The samples prepared in Example <3-1> were heated at 95° C. for 10 minutes, followed by centrifugation (micro 17TR, Hanil) at 15,000 rpm for 1 minute. The evaporated samples were collected. 7.5% polyacrylamide gel was prepared for Western blotting. The samples were loaded on the gel by 20 μl, followed by electrophoresis (Bio-rad). In the meantime, nitrocellulose membrane and filter paper were activated by placing them in the mixed solution comprising 20 Ml of 10× Tris/glycine buffer (25 mM Tris, 192 mM glycine, pH 8.3, Bio-rad), 40 Ml of MeOH and 140 Ml of distilled water.

The electrophoresed polyacrylamide gel was transferred onto the nitrocellulose membrane by using Semi-Dry Transfer System (Bio-rad). The nitrocellulose membrane was treated with 5% BSA (bovine serum albumin, Sigma) at 4° C. for 8 hours for blocking, followed by washing with TBS-T buffer (Tris buffered saline-NaCl 8 g, KCl 0.2 g, Tris 3 g, Tween 20 0.5 Ml) three times for 10 minutes. Then, the primary antibody (phosphotyrosine:biotin, BD Biosciences) and monoclonal anti-phosphotyrosine (Sigma) were diluted in 5% BSA (bovine serum albumin, Sigma) at the ratio of 1:2000 which were loaded onto the washed nitrocellulose membrane by 10 Ml each, followed by reaction at 4° C. for 8 hours. The nitrocellulose membrane was washed with TBS-T buffer three times for 10 minutes, to which the secondary antibody (Mouse-Pierce) diluted in 5% BSA (bovine serum albumin, Sigma) at the ratio of 1:10000 and streptavidin (Sigma) were added by 10 Ml each, followed by reaction at room temperature for 1 hour. The nitrocellulose membrane was washed with TBS-T buffer three times for 10 minutes, to which the mixed solution comprising 500 μl of each West Femto Luminol/Enhancer Solution and West Femto Stable Peroxide Solution included in West Femto maximum sensitivity substrate (Pierce) was added, followed by reaction at room temperature for 5 minutes. Upon completion of the reaction, the nitrocellulose membrane was analyzed by image analyzer (Las 3000, Fuji film) and phosphorylation signal of 293/KDR induced by MBP-VEGF fusion protein was confirmed.

Figure 3:
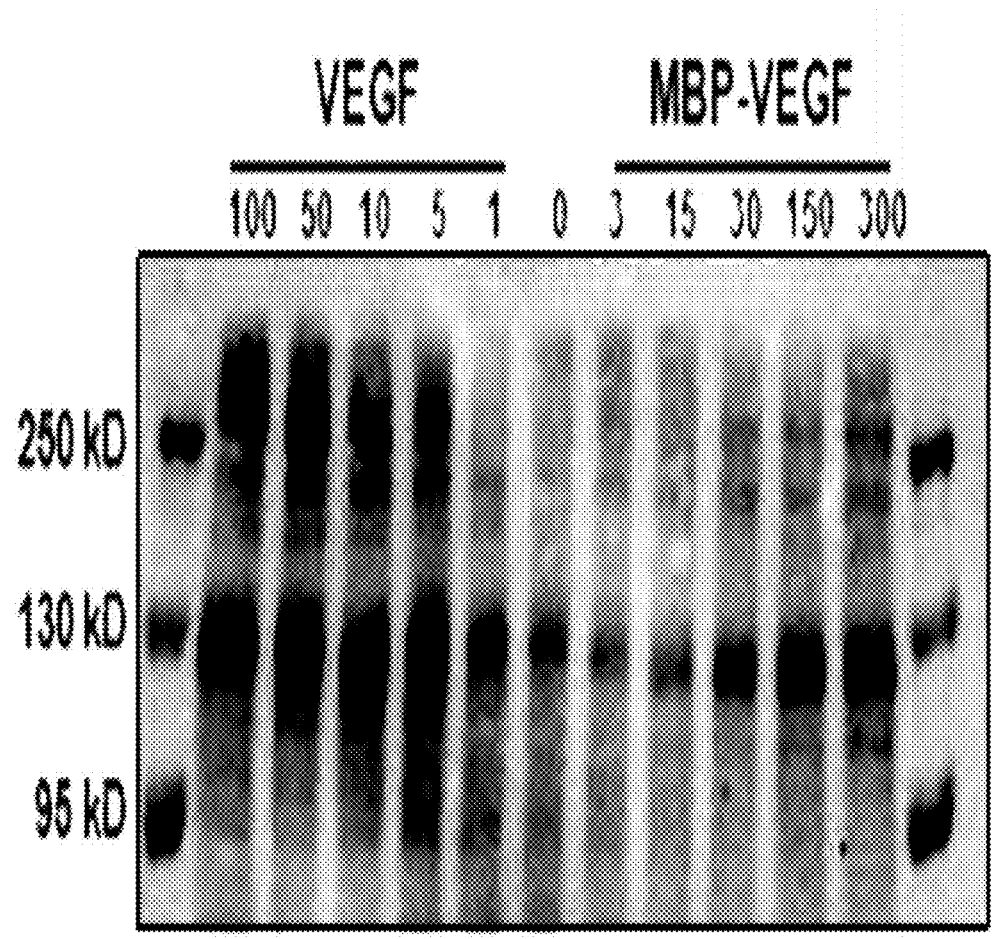
FIG. 3 is a diagram showing the changes of phosphorylation signal in 293/KDR cells treated with the MBP-VEGF fusion protein of the present invention.

As a result, as shown in FIG. 3, phosphorylation was observed in MBP-VEGF fusion protein treated cells dose-dependently at the region of 220 KDa, similar to phosphorylation induced in VEGF treated cells. This phosphorylation pattern was not different from phosphorylation induced in VEGF treated 293/KDR cells by the antibody used in this invention (Backer M V et al., *Biomaterials* 27: 5452-5458, 2006). In addition, in the region of 130 KDa, intracellular phosphorylation was increased dose-dependently.

Example 4

Biochemical Analysis of MBP-VEGF Fusion Protein Immobilization on Polystyrene Surface To investigate the immobilization of MBP-VEGF fusion protein of the present invention on the hydrophobic surface such as polystyrene, MBP-VEGF fusion protein was first treated with biotin as follows. Particularly, 16 μl of 10 mM sulfo-NHS-biotin solution was added to 185 μl of 1 mg/Ml MBP-VEGF fusion protein to make the final volume 0.5 Ml, followed by reaction at room temperature for 1 hour. In the meantime, desalt spin column (Pierce) was washed by the same manner as described in Reference Example 10 and then the reactant was loaded on the washed desalt spin column with which 15 Ml conical tube was conjugated. Centrifugation was performed at 1000×g for 2 minutes to obtain biotin-treated MBP-VEGF fusion protein.

10-10,000 ng/Ml biotin treated MBP-VEGF fusion protein was loaded in a polystyrene 96-well (not for tissue culture, Falcon) at the concentration of 100 μl per well at room temperature for 4 hours, followed by washing with 200 μl of PBS three times. To prevent non-specific binding of MBP-VEGF fusion protein to the polystyrene surface, 200 μl of 1% BSA (bovine serum albumin, Sigma) was added thereto at room temperature for 2 hours, followed by washing with 200 μl of PBS containing 0.05% Tween20 (Amersham Pharmacia Biotech) five times.

100 μl of streptavidin-peroxidase (Sigma) diluted in PBS at the ratio of 1:10,000 was loaded in each well of the 96-well plate on which MBP-VEGF was immobilized, followed by reaction at room temperature for 1 hour. The plate was washed with 200 μl of PBS containing 0.05% Tween 20 five times. Stabilized hydrogen peroxide (R&D Systems) and stabilized tetramethylbenzidine (R&D Systems) were mixed at the ratio of 1:1. 100 μl of the mixed solution was added to each well of the 96-well plate, which was wrapped with aluminum foil, followed by reaction for 20 minutes. 20 minutes later, the reaction was terminated by adding 2 N sulfuric acid solution (50 μl/well). $OD_{450}$ of the 96-well plate was measured by microplate reader (Molecular Device) to confirm the immobilization of MBP-VEGF fusion protein on polystyrene surface.

Figure 4:
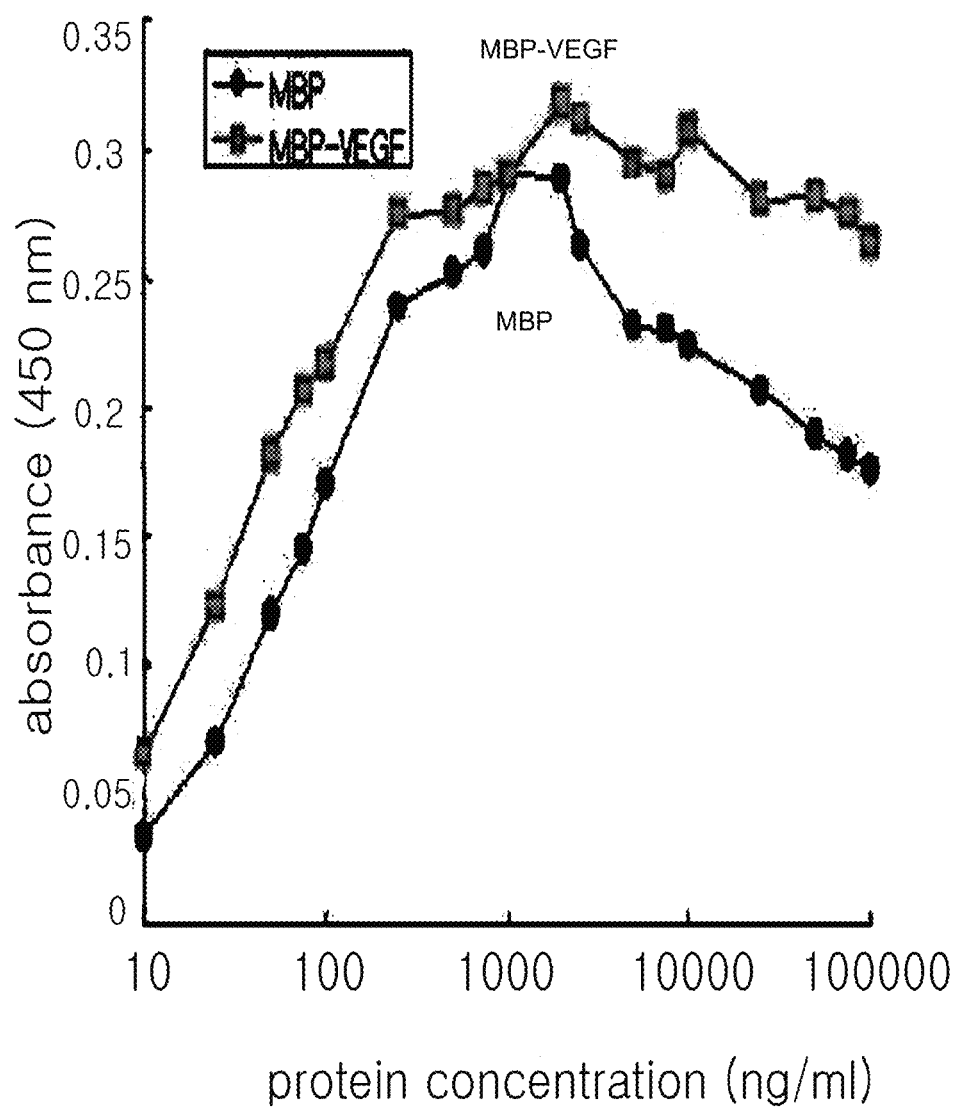
FIG. 4 is a diagram showing the result of biochemical analysis on immobilization of the MBP-VEGF fusion protein of the present invention on the hydrophobic polystyrene surface.

As a result, as shown in FIG. 4, MBP and MBP-VEGF were immobilized on the hydrophobic polystyrene surface dose-dependently at the concentration range of 10-1,000 ng/Ml. However, biochemical analysis of the immobilization is limited to the above concentration range.

Example 5

Physical Analysis of MBP-VEGF Fusion Protein Immobilization on Polystyrene Surface Since biochemical analysis of MBP-VEGF immobilization was limited to a low concentration range as shown in Example 4, immobilization of the fusion protein on the hydrophobic surface at high concentration was investigated by physical method such as quartz crystal microbalance (QCM). QCM is a method to quantify a protein adsorbed based on the fact that when a substance is adsorbed on quartz crystal, frequency is decreased, so that the investigation of the decrease of frequency leads to quantification of the adsorbed protein. In this experiment, quartz crystal was coated with 0.5% polystyrene/toluene solution by spin-coating. As test samples, MBP and MBP-VEGF were diluted in buffer (1 M Tris-HCl 20 Ml, pH 7.5, NaCl 11.7 g, 0.5 M EDTA 2 Ml) and prepared at different concentrations of 1, 10, 50, 100 and 500 μg/Ml. The buffer was running on the quartz crystal for one hour for equilibrium. Then, each sample was running thereon for 15 minutes to make MBP and MBP-VEGF adsorbed on the quartz crystal. Buffer was running on again to eliminate non-adsorbed proteins. Frequency of the quartz crystal was compared before and after adsorption. The adsorbed protein was weighed by Sauerbrey equation ($\Delta f = -\Delta mC/n$) (Hook F, Rodahl M. et al., *Langmuir.* 1998; 14:729-734).

Figure 5:
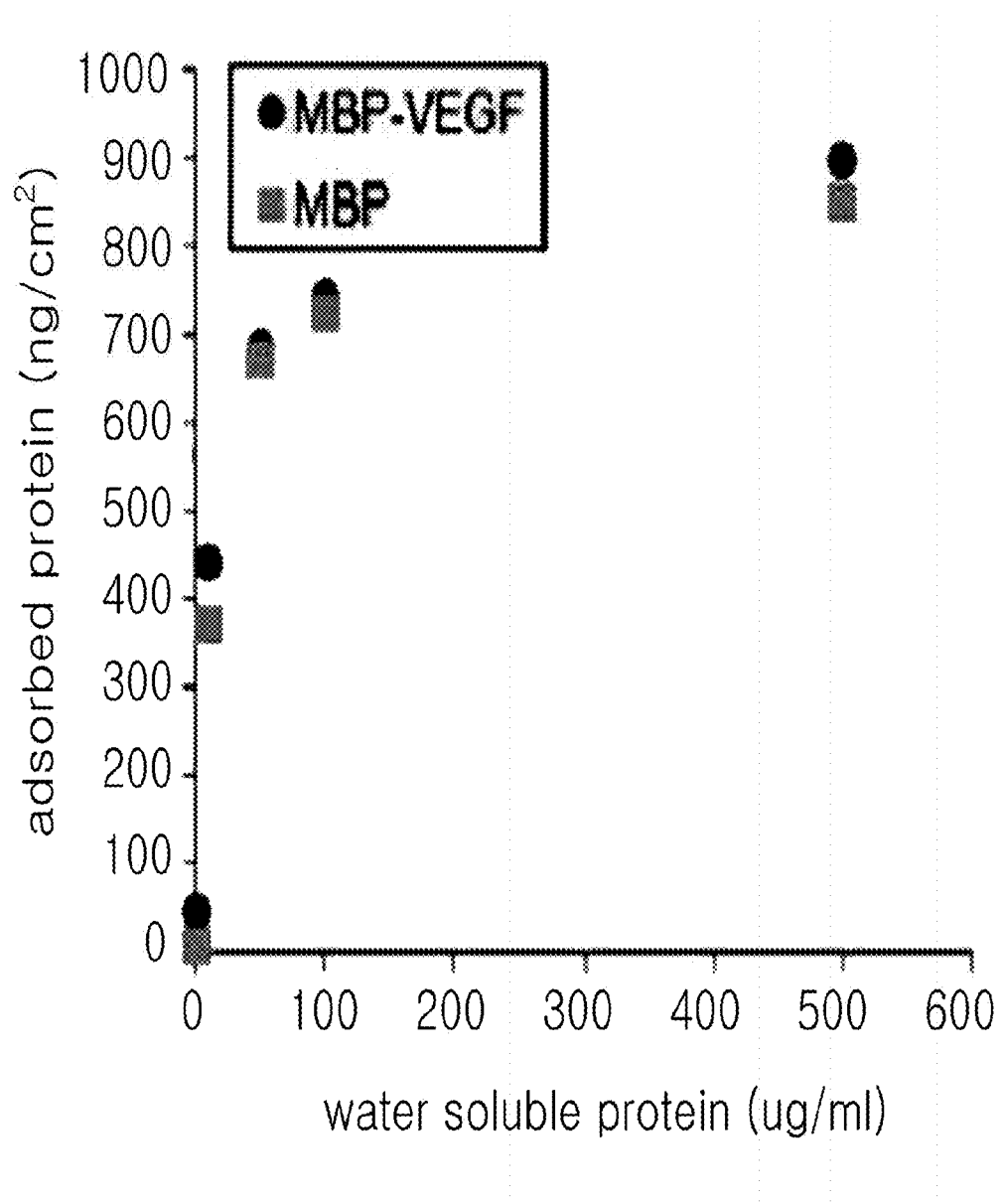
FIG. 5 is a diagram showing the result of physical analysis on immobilization of the MBP-VEGF fusion protein of the present invention on the hydrophobic polystyrene surface.

As a result, as shown in FIG. 5, the MBP-VEGF fusion protein of the present invention was adsorbed on the hydrophobic polystyrene surface dose-dependently at high concentration of 1-500 μg/Ml. This dose-dependent protein adsorption was similar to Langmuir-type monolayer adsorption presenting logarithmic increase.

Example 6

Morphological Changes of 293/KDR Cells by MBP-VEGF Fusion Protein

To investigate the morphological changes of 293/KDR cells by MBP-VEGF fusion protein, the MBP-VEGF fusion protein extracted in Example 2 was filtered in clean bench (Sanyo) by using 0.22 μm syringe filter (Millex GV, Millipore). Then, the filtered fusion protein was added to a polystyrene 96-well plate (not for tissue culture, Falcon) by 100 μl per well at the different concentrations of 0.2, 1 and 10 μg/Ml, which was stood in the clean bench for 4 hours for plate surface coating. Then, the 96-well plate was washed three times with PBS (200 μl/well). To prevent non-specific reaction of 293/KDR cells with the well surface coated with MBP-VEGF fusion protein, 200 μl of 1% BSA (bovine serum albumin, Sigma) was added to some wells, which were treated in clean bench for 2 hours, followed by washing with PBS (200 μl/well) three times.

293/KDR cells were transplanted in the 96-well coated with MBP-VEGF fusion protein at the concentration of $2 \times 10^4$ cells per well. At this time, serum-free DMEM (Welgene) was used. The transplanted cells were cultured in a 37° C. incubator (Thermo) for 45 hours. Then, morphological changes of the cells were observed under phase-contrast microscope (Nikon).

Figure 6:
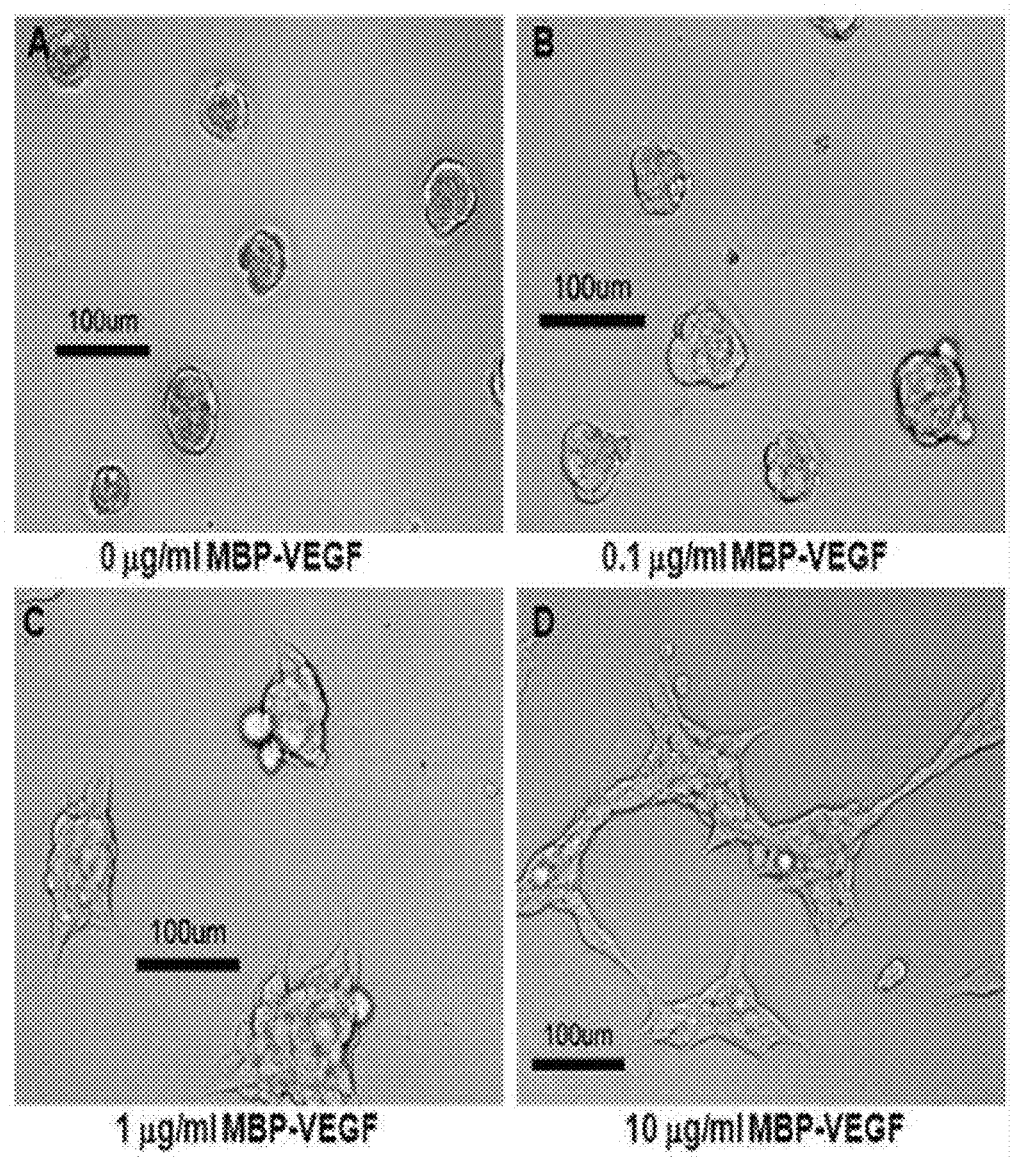
FIG. 6 is a diagram showing the morphological changes of 293/KDR cells cultured in the presence of BSA on the hydrophobic polystyrene surface on which the MBP-VEGF fusion protein of the present invention is immobilized.
Figure 7:
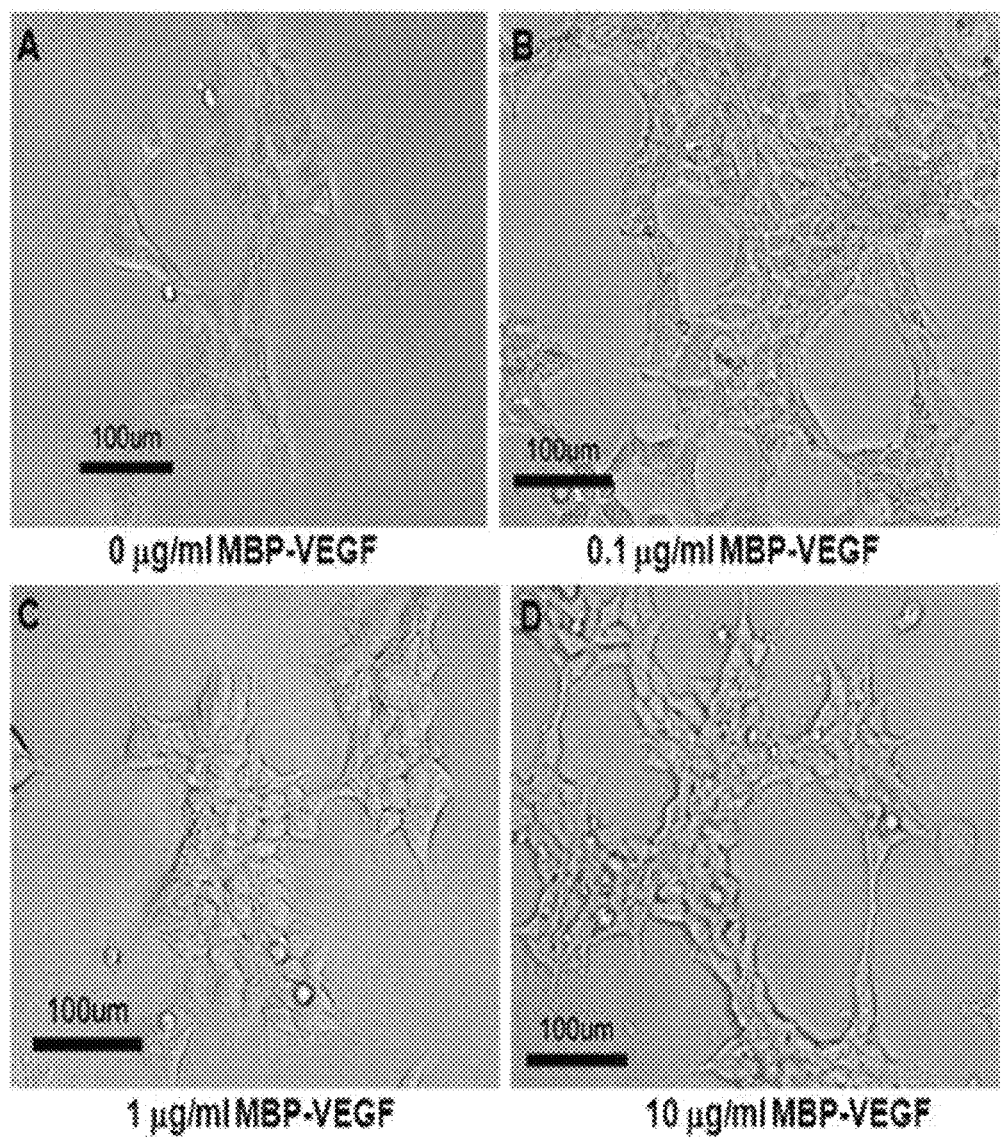
FIG. 7 is a diagram showing the morphological changes of 293/KDR cells cultured in the absence of BSA on the hydrophobic polystyrene surface on which the MBP-VEGF fusion protein of the present invention is immobilized.

FIG. 6 and FIG. 7 illustrate the morphological changes of 293/KDR cells on the hydrophobic polystyrene surface on which MBP-VEGF fusion protein is immobilized in the presence and absence of BSA. FIG. 6 illustrates the result when BSA was treated to the MBP-VEGF adsorbed surface to prevent non-specific cell adhesion. Particularly, on the MBP-VEGF non-adsorbed surface (FIG. 6A), the cells are in spheroid shape. But, as adsorbed MBP-VEGF concentration increased, pseudopodia are formed on the cell dose-dependently, which changes the morphology into long shape (FIGS. 6B-6D). In the meantime, as shown in FIG. 7, When BSA was not treated to the MBP-VEGF adsorbed surface, unlike the MBP-VEGF not adsorbed surface (FIG. 7A) showing even, wide cell growth, pseudopodia were formed on the cell, making the morphology long shape, similarly with the results shown in FIGS. 6B-6D. The above results indicate that it is VEGF of MBP-VEGF fusion protein that is responsible for changes in cell morphology.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for immobilization of a vascular endothelial growth factor (VEGF) on a solid substrate comprising:
    performing PCR reaction with PCR primers of SEQ ID NO: 1 and SEQ ID NO:2 to amplify a nucleic acid sequence encoding VEGF;
    ligating together the amplified nucleic acid sequence encoding VEGF to a nucleic acid sequence encoding maltose binding protein (MBP) to make a nucleic acid sequence encoding a fusion protein of VEGF and MBP, wherein the fusion protein is a VEGF linked to a carboxyl terminal of MBP;
    preparing the fusion protein from the nucleic acid sequence encoding the fusion protein; and
    immobilizing the fusion protein on the hydrophobic surface by physical adsorption of amino terminal containing hydrophobic domain exposed on the surface of MBP on the hydrophobic surface of a solid substrate.

2. The method for immobilization of a VEGF on a solid substrate according to claim 1, further comprising:
    constructing an expression vector containing the nucleic acid sequence encoding the fusion protein;
    transfecting a microorganism with the expression vector; and
    expressing and purifying the fusion protein from the transfected microorganism.

3. The method for immobilization of a VEGF on a solid substrate according to claim 2, wherein the expression vector is for *E. coli*.

4. The method for immobilization of a VEGF on a solid substrate according to claim 2, wherein the microorganism is *E. coli*.

5. The method for immobilization of VEGF on a solid substrate according to claim 2, wherein the fusion protein is purified by maltose specific affinity chromatography.

6. The method for immobilization of a VEGF on a solid substrate according to claim 2, wherein the expression vector is a plasmid.

7. The method for immobilization of a VEGF on a solid substrate according to claim 1, wherein the hydrophobic surface is selected from the group consisting of silanized surface, hydrocarbon coated surface, polymer surface and hydrophobically modified metal surface.

8. The method for immobilization of a VEGF on a solid substrate according to claim 7, wherein the polymer surface is selected from the group consisting of polystyrene, polycarbonate, polypropylene, polyethylene, teflon, polytetrafluoroethylene and polyester containing biodegradable polymers.

9. The method for immobilization of a VEGF on a solid substrate according to claim 7, wherein the hydrophobically modified metal surface is selected from the group consisting of stainless steel, titanium, gold and platinum.

10. The method for immobilization of a VEGF on a solid substrate according to claim 1, wherein the fusion protein is immobilized on the hydrophobic surface at 4-25° C. for 1-24 hours.

11. The method for immobilization of a VEGF on a solid substrate according to claim 1, wherein the VEGF portion of the fusion protein immobilized on the hydrophobic surface is exposed outside on the hydrophobic surface.

12. The method for immobilization of a VEGF on a solid substrate according to claim 1, wherein the VEGF portion of the fusion protein immobilized on the hydrophobic surface exhibits at least 50% original biological activity or functions relative to native VEGF.

13. The method for immobilization of a VEGF on a solid substrate according to claim 1, wherein performing PCR reaction with PCR primers of SEQ ID NO: 1 and SEQ ID NO:2 amplifies the nucleic acid sequence encoding $VEGF_{165}$.

14. The method for immobilization of a VEGF on a solid substrate according to claim 1, wherein performing PCR reaction with PCR primers of SEQ ID NO: 1 and SEQ ID NO:2 amplifies the nucleic acid sequence encoding VEGF using a whole gene extracted from human vascular smooth muscle cells as a template.

\* \* \* \* \*